(12) United States Patent
Zuppiger

(10) Patent No.: US 9,213,011 B2
(45) Date of Patent: Dec. 15, 2015

(54) METHOD AND SYSTEM FOR DISCRIMINATING BULK LIQUID FROM FOAM AND RESIDUALS OF THE BULK LIQUID

(71) Applicant: Roche Diagnostics Operations, Inc., Indianapolis, IN (US)

(72) Inventor: Adelrich Zuppiger, Siebnen (CH)

(73) Assignee: Roche Diagnostics Operations, Inc., Indianapolis, IN (US)

(*) Notice: Subject to any disclaimer, the term of this patent is extended or adjusted under 35 U.S.C. 154(b) by 252 days.

(21) Appl. No.: 13/712,370

(22) Filed: Dec. 12, 2012

(65) Prior Publication Data

US 2013/0160530 A1    Jun. 27, 2013

(30) Foreign Application Priority Data

Dec. 23, 2011    (EP) .................................. 11195460

(51) Int. Cl.
*G01N 27/22* (2006.01)
*G01N 35/10* (2006.01)

(52) U.S. Cl.
CPC ............ *G01N 27/22* (2013.01); *G01N 35/1016* (2013.01); *G01N 2035/1018* (2013.01)

(58) Field of Classification Search
CPC . G01N 27/22; G01N 1/38; G01N 2035/1018; G01N 35/1011; G01N 35/10; G01N 35/1016; G01F 23/26; G01F 23/266; G01F 23/243

USPC ........... 73/61.61, 61.43, 61.44, 61.54, 64.55, 73/304 R, 304 C, 61.41; 324/663

See application file for complete search history.

(56) References Cited

U.S. PATENT DOCUMENTS

| | | | |
|---|---|---|---|
| 6,328,934 B1 | 12/2001 | Ljung et al. | |
| 6,551,558 B1 | 4/2003 | Mann et al. | |
| 6,722,213 B2 | 4/2004 | Offen et al. | |
| 7,150,190 B2 | 12/2006 | Krufka et al. | |
| 2009/0071245 A1* | 3/2009 | Harazin et al. | 73/290 R |
| 2009/0153150 A1* | 6/2009 | Slezak et al. | 324/663 |

\* cited by examiner

*Primary Examiner* — Daniel S Larkin
(74) *Attorney, Agent, or Firm* — Roche Diagnostics Operations, Inc.

(57) ABSTRACT

A method and an automated system for discriminating bulk liquid from foam and/or residuals of the bulk liquid of a sample contained in a sample vessel are presented. A probe having an electric capacitance is provided and moved into the sample. Consecutive steps of charging and at least partially discharging the probe to generate a discharging current is repeatedly performed. A quantity indicative of the discharging current for the consecutive steps of charging and at least partially discharging the probe is measured. The quantity is analyzed to determine an electric resistance ($R_{mess}$) of the sample via the probe. The bulk liquid is discriminated from the foam and/or the residuals of the bulk liquid based on a change of the electric resistance ($R_{mess}$) of the sample occurring when the probe contacts the bulk liquid.

15 Claims, 8 Drawing Sheets

METHOD AND SYSTEM FOR DISCRIMINATING BULK LIQUID FROM FOAM AND RESIDUALS OF THE BULK LIQUID

CROSS-REFERENCE TO RELATED APPLICATIONS

This application is a continuation of EP 11195460.8, filed Dec. 23, 2011, which is hereby incorporated by reference.

BACKGROUND

The present disclosure generally relates to analytical sample processing and, in particular, to a method and an automated system for discriminating bulk liquid from foam which can be present on the bulk liquid of a sample contained in a sample vessel and/or from residuals of the bulk liquid which can be present on the inner side of the sample vessel and/or of a cap for closing the sample vessel.

In automated clinical analyzers, liquid samples, such as bodily fluids, can be tested by various clinical-chemical and immunochemical methods. In practical use, many analytical methods require precise pipetting operations in order to maintain satisfactory analytical accuracy. Usually, pump-controlled probes are used for aspirating and discharging liquids. In order to minimize the danger of cross-contamination and facilitate probe cleaning, it is desirable to position the probe tip just below the liquid surface. The liquid can either be aspirated while keeping the probe stationary or, in case of larger volumes, while lowering the probe further into the vessel so as to maintain the probe tip in the liquid.

In many cases, liquid levels can greatly vary from one liquid vessel to another so that the probe tip has to be reliably positioned within the liquid before starting a pipetting operation. Hence, it is customary to detect the liquid level prior to positioning the probe. In the prior art, liquid level detection is known to be based on various physical principles such as detecting light reflected from the liquid surface or measuring electric characteristics of the probe when put in contact with the liquid.

However, in some cases, especially in the case of liquids which are likely to be subject to foam formation, the reliability of results obtained by conventional liquid level detection techniques can be unacceptably low. For example, when using a technique based on the change of electric capacitance of the probe, the probe is repeatedly charged and discharged using low-frequent electric voltage signals. However, in case foam is present on the bulk liquid, the foam is likely to cause a capacitance change similar to that of the bulk liquid so that there is no clear discrimination between bulk liquid and foam. Accordingly, there is a great risk that the probe will be positioned in the foam instead the bulk liquid resulting in pipetting errors.

Previously, the problem of pipetting errors resulting from foam has been addressed by a method for capacitively determining the uppermost liquid level in which the amount of time required to reach a predetermined voltage value is repeatedly measured for one sample. In order to identify foam, an averaged charging time is requested to exceed a predetermined value. As indicated above, conventional capacitance measurements usually are based on low-frequency voltage signals typically lower than 1 kHz in order to avoid electric impedances. Otherwise, in case of applying high-frequency voltage signals which, for example, are in the range of from 1 MHz to 1 GHz, electric impedances can be generated. Basically, a change of the electric impedance of the probe could be used to discriminate between foam and bulk liquid. However, liquid level detection based on high-frequent impedance measurements requires sophisticated technical equipment and is rather cost-intensive. Furthermore, analyzers based on this technique can cause electric interference effects resulting in low electromagnetic compatibility so that problems with legal provisions may occur. Moreover, in case of employing plural probes, the probes will disturb each other.

Another approach to liquid level detection is given by a measurement of the change of the Ohmic resistance of the probe occurring when the probe tip hits the bulk liquid. While foam can reliably be discriminated from bulk liquid using such technique, the liquid must be in galvanic contact with electric ground which, however, usually is not the case.

Therefore, there is a need to provide an improved method for discriminating between bulk liquid and foam which can reliably be used in case of samples tending to foam formation.

SUMMARY

According to the present disclosure, a method for discriminating bulk liquid from foam and/or residuals of the bulk liquid of a sample contained in a sample vessel is presented. A probe having an electric capacitance can be provided. The probe can be moved into the sample. A pair of consecutive steps of charging and at least partially discharging the probe can be repeatedly performed to generate a discharging current. A quantity indicative of the discharging current for each pair of consecutive steps of charging and at least partially discharging the probe can be measured. The quantity can be analyzed to determine an electric resistance ($R_{mess}$) of the sample via the probe. The bulk liquid from the foam and/or the residuals of the bulk liquid can be discriminated based on a change of the electric resistance ($R_{mess}$) of the sample occurring when the probe contacts the bulk liquid.

In accordance with one embodiment of the present disclosure, the probe can be positioned in the bulk liquid based on the change of the electric resistance ($R_{mess}$) of the sample.

According to the present disclosure, an automated system for discriminating bulk liquid from foam and/or residuals of the bulk liquid of a sample contained in a sample vessel is presented. The automated system can comprise at least one probe having an electric capacitance, a positioning mechanism for moving the probe relative to the sample, a voltage source of a fixed voltage for charging the probe, an electric drain for discharging the probe to generate a discharging current, a controllable switch to alternatively connect the probe to the voltage source or to the drain, an electric circuitry connected to the probe to measure a quantity indicative of the discharging current and a controller to move the probe into the sample, to control the switch to repeatedly perform consecutive steps of charging and at least partially discharging the probe, and to control the electric circuitry to measure the quantity indicative of the discharging current for each pair of consecutive steps of charging and at least partially discharging the probe to determine an electric resistance ($R_{mess}$) of the sample. The bulk liquid can be discriminated from foam and/or residuals of the bulk liquid based on a change of the electric resistance ($R_{mess}$) of the sample occurring when the probe contacts the bulk liquid.

Accordingly, it is a feature of the embodiments of the present disclosure to provide an improved method for discriminating between bulk liquid and foam which can reliably be used in case of samples tending to foam formation. Other features of the embodiments of the present disclosure will be apparent in light of the description of the disclosure embodied herein.

BRIEF DESCRIPTION OF THE SEVERAL VIEWS OF THE DRAWINGS

The following detailed description of specific embodiments of the present disclosure can be best understood when read in conjunction with the following drawings, where like structure is indicated with like reference numerals and in which.

DETAILED DESCRIPTION

Figure 1:
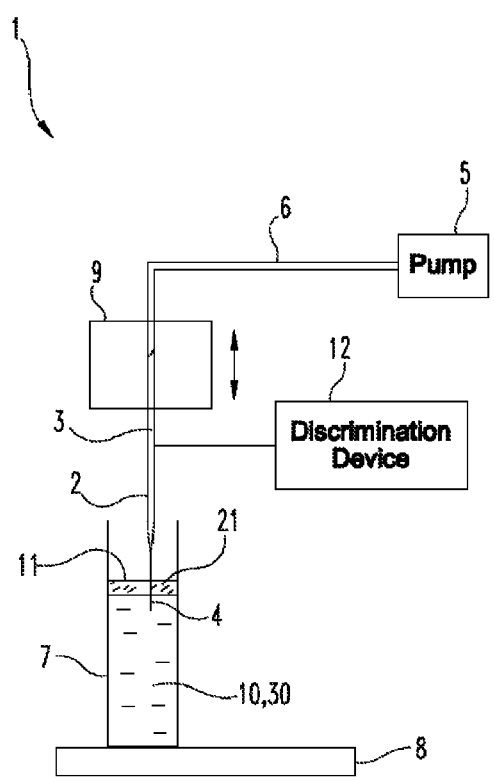
FIG. 1 illustrates a system provided with a probe for discriminating between bulk liquid and foam and/or residuals of the bulk liquid of a sample contained in a sample vessel according to an embodiment of the present disclosure.

In the following detailed description of the embodiments, reference is made to the accompanying drawings that form a part hereof, and in which are shown by way of illustration, and not by way of limitation, specific embodiments in which the disclosure may be practiced. It is to be understood that other embodiments may be utilized and that logical, mechanical and electrical changes may be made without departing from the spirit and scope of the present disclosure.

A new method for discriminating between bulk liquid and foam which can be present on the bulk liquid of a sample contained in a sample vessel and/or for discriminating between bulk liquid and residuals of the bulk liquid which can be present on the inner side of the sample vessel and/or a cap for closing the sample vessel is proposed.

As used herein, the term "sample" can denote any fluid of interest which, for example, can be subject to foam formation. Specifically, samples in the sense of the term can include non-biological fluids such as, but not limited to, reagents, dilutants, buffers and suspensions of magnetic particles which, for example, can be used for nucleic acid purification purposes.

Samples can also be or at least contain components of biological fluids such as, but not limited to, body fluids, for example, blood, serum, urine, milk, saliva and cerebrospinal fluids. Specifically, samples in the sense of the term can be subject to analyses and assays in medical and pharmaceutical research and diagnosis including clinical-chemical analysis and/or immunochemical and/or biochemical analysis items. Samples can, for example, be subject to in-vitro amplification techniques based on the polymerase chain reaction or any other reaction of the nucleic acid amplification type.

A sample can contain bulk liquid free of (macroscopic) gas bubbles and may optionally contain foam present on the liquid surface of the bulk liquid and/or residuals of the bulk liquid present on the inner side of the sample vessel and, if the case may be, of a cap for closing the sample vessel. Contrary to the bulk liquid, foam can contain one or more gas bubbles. In the more strict sense of the term, foam can contain a plurality of small gas bubbles, the diameter of which can be smaller than the dimension of the (horizontal) cross-section of the sample vessel. Alternatively or additionally, foam can include a so-called "segment region" which can contain a smaller number (for example, less than ten) of gas bubbles having a larger diameter which may even be as large as the dimension of the (horizontal) cross-section of the sample vessel. Such segment region can typically occur when the sample vessel is tilted over and then is brought in an upright position. As used herein, the term "residuals" of bulk liquid can relate to portions, or traces, of the bulk liquid which can be present on the inner side of the sample vessel such as, but not limited to, a wetting layer and/or on the inner side of a cap for closing the sample vessel such as, but not limited to, one or more drops.

The method for discriminating between bulk liquid and foam and/or residuals of the bulk liquid can comprise providing a probe to be positionable with respect to the sample so that the probe can be moved into and out of the bulk liquid. Specifically, being capacitively coupled to the ambient, the probe can have an electrostatic capacitance and thus can be charged by applying an electric potential thereto. Typically, the probe can be made of an electrically conductive material such as, but not limited to, a metallic material, a conductive plastic material, and an isolating material that can be combined with a conductive material. The probe can be moved into the sample.

The method can comprises repeatedly performing a pair of consecutive steps of charging the probe by applying an electric voltage (potential) thereto, and at least partially, in particular fully, discharging the probe by applying a smaller voltage (potential) thereto or by connecting the probe to electric ground so as to generate a discharging current.

The method can comprise measuring a quantity indicative of (i.e. related to) the discharging current for each pair of consecutive steps of charging and at least partially discharging the probe simultaneously with discharging the probe. In one embodiment, the quantity indicative of the discharging current can be an electric voltage signal and/or a time derivative thereof. The electric signal can, for example, be sampled during a sampling period. In one alternative embodiment, the quantity indicative of the probe discharging current can be a time interval required for fully discharging the probe so that the time required for discharging the probe can be measured simultaneously with discharging the probe. The method can comprise analyzing the above-captioned quantity to determine an electric resistance of the sample as given by the bulk liquid and/or foam and/or residuals of the bulk liquid, via the probe. The method can comprise discriminating bulk liquid from foam and/or residuals of the bulk liquid based on a change of the electric resistance of the sample occurring when the probe tip contacts the bulk liquid.

The electric resistances of bulk liquid, foam and residuals of the bulk liquid normally can be largely different with respect to each other so that the method can enable a clear and distinct discrimination between bulk liquid and foam as well as between bulk liquid and residuals of the bulk liquid. Accordingly, the probe can reliably be positioned within the bulk liquid. As a result, liquid contained in the sample vessel can be reliably aspirated by the probe enabling an accuracy of the extracted liquid volume as high as reasonably possible.

Repeatedly determining the electric resistance of the sample preferably can be performed simultaneously with moving the probe into the sample so as to position the probe with respect to the sample.

In one embodiment, determining the electric resistance of the probe can be periodically repeated with a repeating frequency in a range of from about 1 kHz to about 100 kHz. This frequency range can be advantageous in that inductances can be neglected. On the other hand, analysis of the electric voltage signal can be obtained when discharging the probe can be facilitated due to the flank steepness of the voltage signal resulting in especially high accuracy.

In one embodiment, the quantity indicative of the discharging current can be an electric voltage signal and/or a time derivative thereof. In that case, it can be preferred that the voltage signal be analyzed in a time interval starting with discharging the probe wherein the voltage signal can be analyzed with respect to a voltage drop when starting discharging the probe.

Accordingly, the electric resistance of the sample when the probe is galvanically coupled to bulk liquid, foam or residuals of the bulk liquid can be determined in reliable manner to discriminate bulk liquid from foam and residuals of the bulk liquid.

The method can allow for a clear discrimination between bulk liquid and foam which can be present on the liquid surface of the bulk liquid as well as between bulk liquid and residuals of the bulk liquid which can be present on the inner wall of the sample vessel and/or the inner side of a cap for closing the sample vessel. Since a change of electric resistance of the sample can be observed when the probe contacts the bulk liquid the liquid level of the sample can also readily be determined.

In one embodiment, the method can also comprise determining a change of the electric capacitance of the probe when lowering into the sample. This can be useful in some cases, especially in the case of small liquid volumes.

A method for positioning a probe having an electric capacitance for performing pipetting operations on a sample is also disclosed. The probe can be provided. The probe can be moved into the sample. A pair of consecutive steps of charging and at least partially discharging the probe can be repeatedly performing to generate a discharging current. A quantity indicative of the discharging current for each pair of consecutive steps of charging and at least partially discharging the probe can be measured. The quantity can be measured to determine an electric resistance of the sample. Bulk liquid can be discriminated from foam and/or residuals of the bulk liquid based on a change of the electric resistance of the sample occurring when the probe tip contacts the bulk liquid. The probe can be positioned in the bulk liquid based on the change of the electric resistance of the sample.

In one embodiment, the probe can be lowered into the bulk liquid, followed by performing a pump-controlled pipetting operation so as to suck-in or discharge liquid. The probe can be kept stationary while performing the pipetting operation and/or can moved further into the sample vessel simultaneously therewith so as to keep the probe in the bulk liquid.

A new automated system for discriminating bulk liquid from foam and/or residuals of the bulk liquid of a sample contained in a sample vessel is proposed. The system can be configured in various ways in accordance with specific demands of the user and, for example, can be part of an automated analyzer related to various analysis items such as, but not limited to, clinical-chemical, biochemical, immunochemical analysis items. The system can include at least one probe to be positionable with respect to the sample. Due to capacitive coupling to the ambient, the probe can have an electric capacitance.

The system can further include a positioning mechanism for positioning the probe relative to the sample, for example, moving the probe into and out of the bulk liquid. In one embodiment, the probe can be made of or at least comprise an electrically conductive material. It can yet further include a voltage source of a fixed voltage for charging the probe and an electric drain for discharging the probe.

The system can further include a controllable switch, such as, for example, a transistor, to alternatively connect the probe to the voltage source for charging the probe or to the electric drain such as, for example, electric ground, for at least partially (e.g. fully) discharging the probe to generate a discharging current.

The system can further include an electric circuitry connected to the probe to determine a quantity indicative of (related to) the discharging current. In one embodiment, the electric circuitry can comprise a sample-and-hold device for sampling an electric voltage signal of the probe and/or a differentiating device for differentiating the electric voltage signal of the probe.

The system can further include a controller to move the probe into the sample, to control the switch to repeatedly perform consecutive steps of charging and at least partially discharging the probe, and to control the electric circuitry to measure the quantity indicative of the discharging current for each pair of consecutive steps of charging and at least partially discharging the probe to determine an electric resistance of the sample. The bulk liquid can be discriminated from foam and/or residuals of the bulk liquid based on a change of the electric resistance of the sample occurring when the probe contacts the bulk liquid.

The system can thus allow for a robust discrimination of bulk liquid and foam and/or residuals of the bulk liquid by detecting an electric resistance of the sample via the probe. It can also allow for a detection of the liquid surface, that is to say, liquid level.

One advantage can be that, in contrast to the prior art techniques, the electric resistance of the sample can reliably be used to detect the bulk liquid even in case foam is present on the liquid surface of the bulk liquid and/or residuals of the bulk liquid are present on the inner side of the sample vessel and/or cap for closing the sample vessel. Hence, bulk liquid of any sample which, e.g., can be subject to foam formation can reliably be detected.

In one embodiment, the probe can perform pipetting operations similar to a pipette so as to withdraw or discharge liquids when generating a negative or positive pressure therein. The probe can thus have a double functionality of discriminating between bulk liquid and foam and/or between bulk liquid and residuals of the bulk liquid and pipetting liquids. Hence, pipetting operations can be combined with an exact positioning of the probe within the bulk liquid. The probe can be lowered into the bulk liquid so as to withdraw or dispense definite liquid volumes. The probe for pipetting liquids can, for example, be embodied as needle made of metallic material such as, for example, a steel needle.

In one embodiment, the sample vessel for containing the sample can comprise a vessel portion made of an electrically conductive material. The conductive vessel portion can be supported by an electrically conductive support, such as, for example, an electrically conductive work-plate, in electric contact therewith. As a result, the capacitive coupling between the probe and the ambient, for example, support of the sample vessel can be improved.

In one embodiment, the vessel for containing the sample can be made of isolating material and can be accommodated in a vessel envelope made of an electrically conductive material. The conductive vessel envelope can be supported by an electrically conductive support, such as, for example, an electrically conductive work-plate, in electric contact therewith. As a result, the capacitive coupling between the probe and the ambient, for example, support of the vessel can be improved.

Referring initially to FIG. 1, an exemplary embodiment of an automated system for discriminating between bulk liquid 10 and foam 21 and/or residuals 48 of the bulk liquid 10 of a liquid sample 30 contained in a sample vessel 7 is illustrated. The automated system 1 can include a probe 2, such as, for example a pipette for performing pipetting operations, i.e., aspirating and dispensing liquids. Specifically, the probe 2 can be provided with an inner (fluid) channel 3 with a probe tip 4 that can open to ambient air. At an opposite side thereof, the probe 2 can be fluidically connected to a pump 5 by a pump conduit 6 for generating a negative or positive pressure in the channel 3 so that liquids can be sucked-in or discharged according to the specific demands of the user. Since pumps for operating pipettes are well-known to those of skill in the art, e.g., from commercially available analyzers, the pump 5 is not further elucidated herein.

The probe 2 can, for example, be configured as needle made of metallic material such as, for example, stainless steel, and can have a sharpened probe tip 4 for facilitating penetration of a cap (not shown) in the case of a top-closed sample vessel 7. While only one probe 2 is shown for the purpose of illustration, those of skill in the art can recognize that more than one probe 2 can be envisaged according to the specific demands of the user.

With continued reference to FIG. 1, in the system 1, the probe 2 can be used to aspirate liquid contained in the sample vessel 7 placed on a horizontal work-plate 8. Accordingly, the sample vessel 7 can receive a sample 30 of interest such as a bodily fluid, for example, blood, urine or the like. The sample vessel 7 can, for example, be an individual tube or vial or as one well of a multi-well plate.

As illustrated in FIG. 1, foam 21 can be present on the liquid surface 11 of the bulk liquid 10 of the sample 30 so that the probe tip 4 can be placed within the bulk liquid 10 in order to avoid pipetting errors caused by aspirating foam.

The probe 2 can be made of an electrically conductive material such as, for example, a metallic material like stainless steel. Being made of electrically conductive material, the probe 2 can have an intrinsic electrostatic capacitance $C_{mess}$ by being capacitively coupled to the ambient, for example, to the work-plate 8 which, for example can also be made of electrically conductive material. Accordingly, the probe 2 can be charged or discharged depending on the capacitive coupling to the ambient.

With continued reference to FIG. 1, the system 1 can further include an automated positioning mechanism 9 for positioning the probe 2 with respect to the sample 30 contained in the sample vessel 7. The positioning mechanism 9 can, for example, vertically translate the probe 2 towards and away from the sample 30 while keeping the sample vessel 7 stationary with respect to the work-plate 8 as illustrated by the double-headed arrow. Since such positioning mechanism 9 is well-known to those of skill in the art, e.g., from commercially available analyzers, it is not further elucidated herein.

Operating the positioning mechanism 9, the probe 2 can be vertically lowered to reach a position where the probe tip 4 can dip into the bulk liquid 10 to perform pipetting operations. Particularly, the probe tip 4 can be positioned a small distance below the liquid surface 11 in order to minimize the contact between the sample 30 and the probe 2. By placing the probe tip 4 in the bulk liquid 10 pipetting operations can reliably be performed.

In the case of the probe tip 4 being lowered into the sample 30, a change of the electric capacitance $C_{mess}$ of the probe 2 can be observed. In the case of the probe 2 dipping into the sample 30, the capacitance $C_{mess}$ of the probe 2 can be altered by the electric capacitances of the bulk liquid 10 and foam 21, respectively.

In the case of the probe tip 4 being lowered into the sample 30, a change of the electric resistance $R_{mess}$ of the sample 30 can also be observed. In the case of the probe 2 dipping into the sample 30, the electric resistance $R_{mess}$ of the sample 30 can be varied depending on the electric connection (galvanic coupling) between the probe 2 and the bulk liquid 10 and between the probe 2 and foam 21, respectively.

With continued reference to FIG. 1, in the system 1, the probe 2 can be electrically connected to a discrimination device 12 which can discriminate between the bulk liquid 10 and foam 21 and between bulk liquid 10 and residuals 48 (illustrated in FIG. 2) of the bulk liquid 10 of a sample 30 contained in the sample vessel 7.

Figure 2:
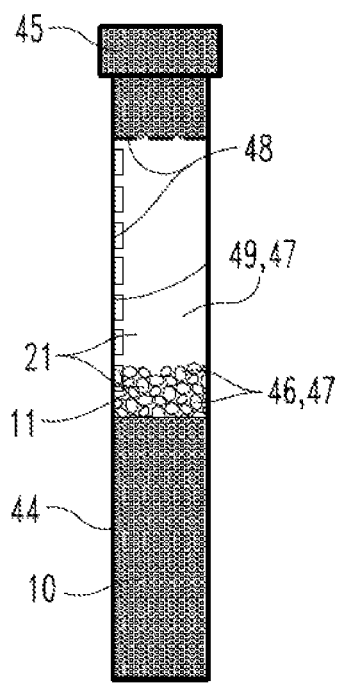
FIG. 2 illustrates an exemplary sample vessel containing sample according to an embodiment of the present disclosure.

With reference to FIG. 2, the sample vessel 7 can, for example, be a top-closed tube 44 provided with a cap 45 pressed into tube 44 for fixing. As indicated above, the sample 30 can comprise the bulk liquid 10 wherein foam 21 can be present on the liquid surface of the bulk liquid. As can be seen in FIG. 2, in some cases, the foam 21 can include a first (lower) foam zone 46 having many small bubbles 47 having the diameter smaller than the diameter of the tube 44 and a second (upper) foam zone 49 (the "segment region") which can comprise of one or more very large bubbles 47 often expanding across the whole diameter of the tube 44. While the first foam zone 46 can typically be a result of shaking or stirring the sample 30, the second foam region 49 can likely be generated when the top-closed tube 44 is tilted and then brought in an upright position again. Furthermore, residuals 48 of the bulk liquid 10 can be present on the inner side of the tube 44 and/or the cap 45 such as a wetting layer on the inner side of the tube 44 and drops on the inner side of the cap 45. Such residuals 48 can be the result of tilting the tube 44 and then placing it in an upright position. Hence, the term "sample" as used herein includes both the bulk liquid 10 (non-foamy portion of the sample 30), the foam 21 (foamy portion of the sample 30) on the liquid surface 11 of the bulk liquid 10 and the residuals 48 of the bulk liquid 10.

Figure 3:
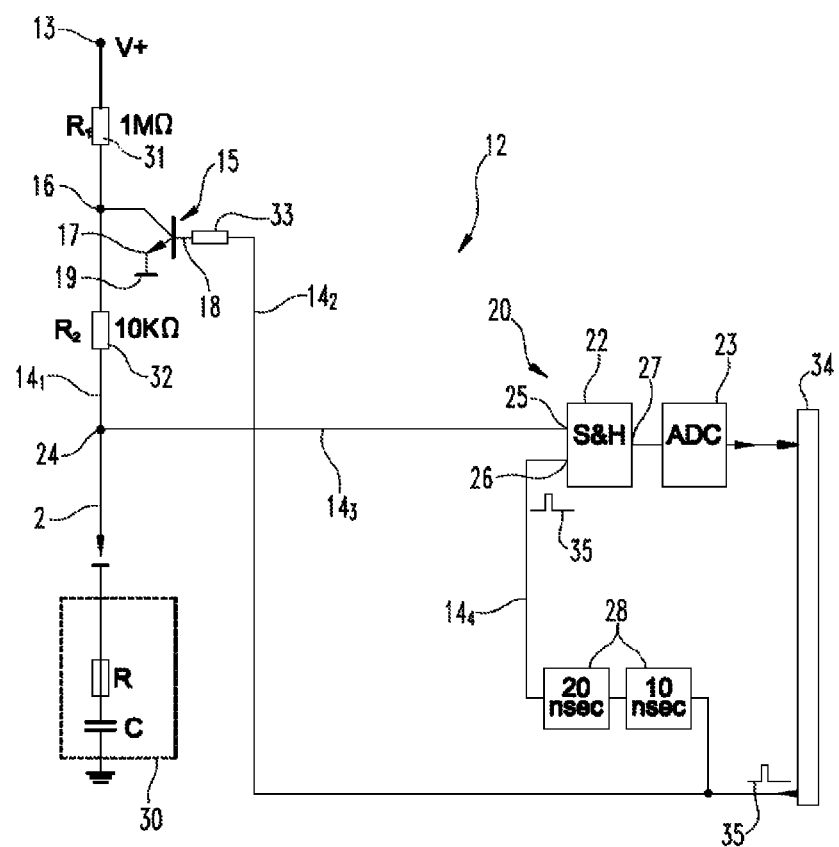
FIG. 3 illustrates an exemplary embodiment of the system of FIG. 1 according to an embodiment of the present disclosure.

With reference to FIG. 3, in one exemplary embodiment of the system 1, the discrimination device 12 can include a voltage source 13 of a fixed voltage (V+) electrically connected to the probe 2 by a first electric line $14_1$ via a first resistor 31 having an electric resistance $R_1$ and a second resistor 32 having an electric resistance $R_2$ serially arranged with respect to each other within the first electric line $14_1$. The voltage source 13 can, for example, be a fixed voltage (for example, positive potential) of about 24 Volts. In the embodiment shown, the first resistor 31 can have a much larger electric resistance than the second resistor 32, the first resistance $R_1$, for example, being as large as about 1 MΩ, the second resistance $R_2$, for example, being about 10 kΩ.

As illustrated in FIG. 3, the discrimination device 12 can further include an electronic switch, such as, for example, a transistor 15 such as, for example, a bipolar transistor. Specifically, a collector contact 16 of the transistor 15 can be connected to the first electric line 14₁ in a position in-between the first and second resistors 31, 32 and an emitter contact 17 thereof can be connected to electric ground 19. Furthermore, a base contact 18 of the transistor 15 can be electrically connected to a microprocessor-based controller 34 by a second electric line 14₂ via a third resistor 33 having a small electric resistance $R_3$ of, for example, about 1 kΩ.

The controller 34 can provide the base contact 18 with an electric clock signal 35 having periodically repeated switching pulses such as, for example, periodic square wave (voltage) pulses as illustrated in FIG. 3. When applying voltage pulses of the electric clock signal 35 to the base contact 18, the transistor 15 can be periodically switched on or off. In the transistor's on-state, the path between the collector contact 16 and the emitter contact 17 can be electrically conductive so that an electric current can flow from the first electric line 14₁ to the emitter contact 17-connected electric ground 19 as indicated by the arrow. Otherwise, in the transistor's off-state, the electric path between the collector contact 16 and the emitter contact 17 can be highly resistive so that the first electric line 14₁ can be electrically separated from the electric ground 19. Accordingly, by switching the transistor 15 in on-state or off-state, the probe 2 can either be connected to the voltage source 13 or to electric ground 19.

As is further illustrated in FIG. 3, the discrimination device 12 can include an electric circuitry 2 to determine the electric resistance of ($R_{mess}$) of the sample 30 and the electric capacitance ($C_{mess}$) of the probe 2. In the case where the probe tip 4 is outside the sample 30, since neither the bulk liquid 10 nor the foam 21 or residuals 48 of the bulk liquid 10 are galvanically coupled to the probe 2, the electric resistance ($R_{mess}$) measured can correspond to the intrinsic electric resistance of the probe 2 due to fact that the probe 2 is located in a gaseous atmosphere normally can be neglected. Otherwise, in the case where the probe tip 4 dips into the sample 30, the measured electric resistance ($R_{mess}$) can be altered by the galvanic coupling between probe 2 and sample 30.

In one exemplary embodiment, as illustrated in FIG. 3, the electric circuitry 20 can include a sampling device 22 can be a sample-and-hold device for sampling an electric voltage (potential) of the probe 2 when the probe 2 is charged or discharged depending on the transistor's on- or off-states. Correspondingly, a first sampling device input 25 can be electrically connected to the probe 2 via the first electric line 14₁ by a third electric line 14₃. Specifically, a sampling device contact 24 can contact the first electric line 14₁ in a position in-between the collector contact 16 and the probe 2. Furthermore, a sampling device output 27 can be electrically connected to the controller 34 via an analog-digital converter 23 for converting analog signals to digital signals.

A second sampling device input 26 can be connected to the second electric line 14₂ by a fourth electric line 14₄ so that the sampling device 22 can receive the (slightly modified) clock signal 35. Hence, the sampling device 22 can be operated synchronously with the transistor 15 except from a predetermined short time delay imposed on the voltage pulses by a delay circuitry 28 included in the fourth electric line 14₄. The delay circuitry 28 can, for example, delay the voltage pulses by a time shift of about 10 nsec so as to account for the non-zero switching times of the transistor 15. Furthermore, the sampling periods can be selectively adapted to the switching periods.

As a result, the sampling device 22 can be operated to sample the voltage signals of the probe 2 and can hold its value at a constant level for a specified time interval. For this purpose, the sample-and-hold circuitry can typically include a capacitor (not shown) connected to the probe 2, wherein the capacitor can be connected to a buffer amplifier (not shown) via a switch (not shown) for charging or discharging the capacitor. The analog-digital converter 23 can be used to convert the analog signals to digital signals for further processing by the controller 34.

With reference to FIG. 3, when dipping the probe tip 4 into the sample 30 contained in the sample vessel 7, the electric resistance ($R_{mess}$) of the sample 30 as measured by the electric circuitry 20 can change from the intrinsic electric resistance of the probe 2 (which can be neglected) to the electric resistance of the sample 30 as given by the electric resistances of bulk liquid 10, foam 21 and residuals 48, respectively. Due to the fact that in many cases the electric resistance of the foam 21 can be much higher than that of the bulk liquid 10, bulk liquid 10 and foam 21 can be reliably discriminated by determining the electric resistance ($R_{mess}$) of the sample 30. Furthermore, due to the fact that in many cases the electric resistance of the residuals 48 of the bulk liquid 10 can be much higher than that of the bulk liquid 10, bulk liquid 10 and residuals 48 of the bulk liquid 10 can be reliably discriminated by determining the electric resistance ($R_{mess}$) of the sample 30.

Otherwise, when dipping the probe tip 4 into the sample 30 contained in the sample vessel 7, the electric capacitance as measured by the electric circuitry 20 can change from the intrinsic capacitance ($C_{mess}$) of the probe 2 to a capacitance modified by the capacitance of the sample 30. Depending on the specific sample, the capacitance of the bulk liquid 10 can differ from the capacitance of the foam 21 and/or residuals 48. However, it can also be rather similar thereto so that the bulk liquid 10 and the foam 21 and/or residuals 48 cannot always be reliably discriminated by the change of capacitance observed when the probe tip 4 dips into the sample 30.

Figure 4:
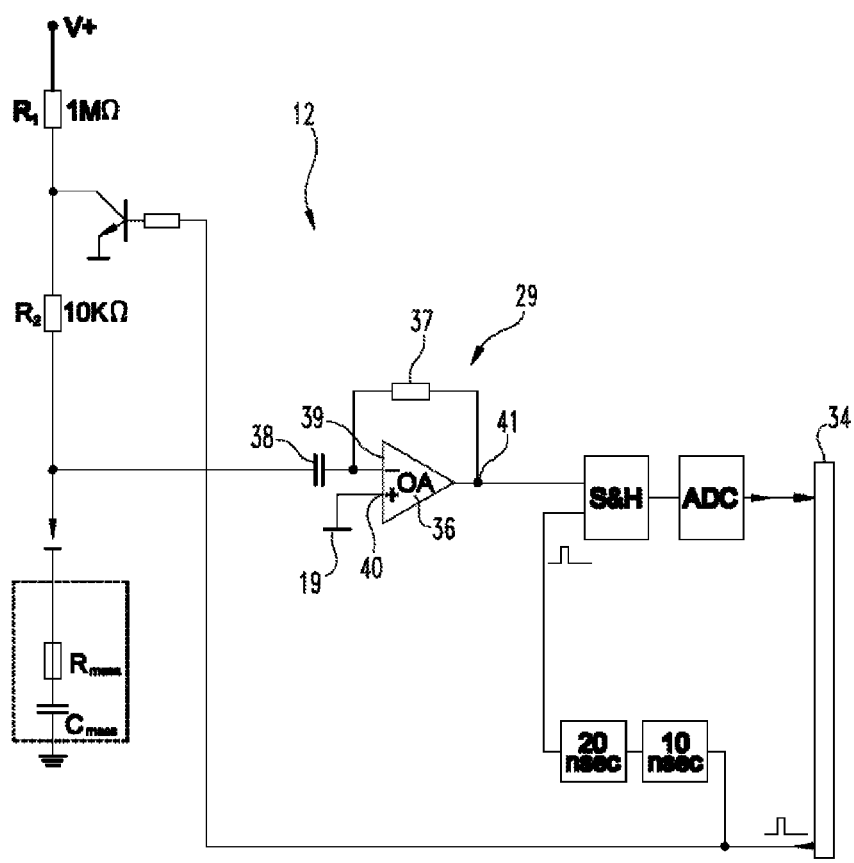
FIG. 4 illustrates another exemplary embodiment of the system of FIG. 1 according to an embodiment of the present disclosure.

With reference to FIG. 4, in another embodiment of the system 1, the third electric line 14₃ connecting the sampling device 22 with the probe 2 and the first electric line 14₁, can respectively, include a differentiating device 29 for determining a time derivative of the electric voltage of the probe 2. As is known to those of skill in the art, the differentiating device 29 can usually comprise an operational amplifier 36, a fourth resistor 37 and a capacitor 38 wherein a first amplifier input 39 can be connected to the probe 2 via third electric line 14₃ and capacitor 38 and a second amplifier input 40 can be connected to electric ground 19. Furthermore, an amplifier output 41 can be connected to the first amplifier input 39 via the fourth resistor 37. Accordingly, current flowing through the capacitor 38 can be proportional to the time derivative of the voltage across the capacitor 38. Otherwise, the voltage across the fourth resistor 37 can be proportional to the time derivative of the voltage across the capacitor 38. Hence, in contrast to the embodiment of FIG. 3, the time derivative of the electric voltage of the probe 2 can be sampled by the sampling device 22. The other components of the system 1 can be similar to those in FIG. 3.

Figure 5A:
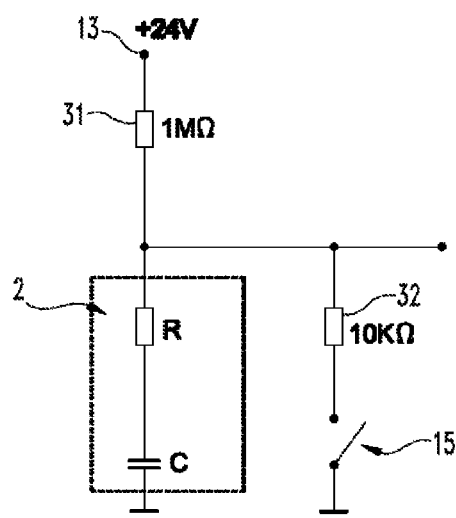
FIGS. 5A-B illustrate a method for discriminating between bulk liquid and foam and/or residuals of the bulk liquid using the system of FIG. 1 according to an embodiment of the present disclosure.
Figure 5B:
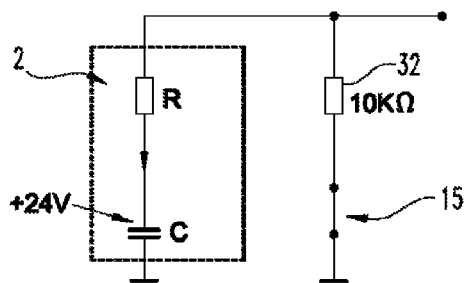

With reference to FIGS. 5A and 5B, a process for discriminating between bulk liquid 10 and foam 21 and/or residuals 48 of the bulk liquid 10 of the sample 30 contained in the vessel 7 is explained. In this process, a pair of two consecutive steps I and II can be multiply repeated when lowering the probe 2 so as to dip the probe tip 4 into the sample 30.

As illustrated in FIG. 5A, in the first step I, the transistor 15 can be brought in its off-state (opened state), for example, corresponding to the time period between two adjacent voltage pulses of the clock signal 35 applied to the base contact 18. The electric potential of the voltage source 13 can be applied to the probe 2 charging the probe 2 to an extent given by the electric capacitance of the probe 2. Depending on the time period between two adjacent voltage pulses of the clock signal 35, the probe 2, for example, can be charged until saturation is reached.

As illustrated in FIG. 5B, in the second step II, the transistor 15 can be brought in its on-state (closed state), for example, corresponding to the time period of applying a voltage pulse of the clock signal 35 to the base contact 18 so that the probe 2 which has been charged in the first step I can be electrically connected to ground 19 causing a discharge current to flow from the probe 2 to electric ground 19. During discharge of the probe 2, the voltage signal caused by the discharge current and/or a time derivative thereof can be sampled by the sampling device 22 so that the electric resistance $R_{mess}$ of the sample 30 can be determined. Due to the fact that the electric resistance $R_{mess}$ of the sample 30 can be greatly different in the case where the probe tip 4 is in the bulk liquid 10 or in the foam 21 and residuals 48, respectively, the bulk liquid 10 can be reliably discriminated from the foam 21 and residuals 48 of the bulk liquid 10. A characteristic change of the electric resistance $R_{mess}$ of the sample 30 can be observed when the probe tip 4 is lowered from the foam 21 into the bulk liquid 10, that is to say, when the probe tip 4 hits the liquid surface 11.

In order to position the probe tip 4 within the bulk liquid 10, the pair of first and second steps I, II can periodically repeated as defined by a periodic repetition of voltage pulses of the clock signal 35 applied to both the transistor 15 and the electric circuitry 20. In one embodiment, the clock signal 35 can have a frequency of about 1 kHz to about 100 kHz so that parasitic electric inductances can be avoided to a large extent. The above process can also be used to detect the liquid surface 11 of the bulk liquid 10 by detecting the actual position of the probe tip 4 at which the probe tip 4 hits the liquid surface 11 of the bulk liquid 10, i.e., when the characteristic change of the electric resistance $R_{mess}$ of the sample 30 occurs.

Figure 6:
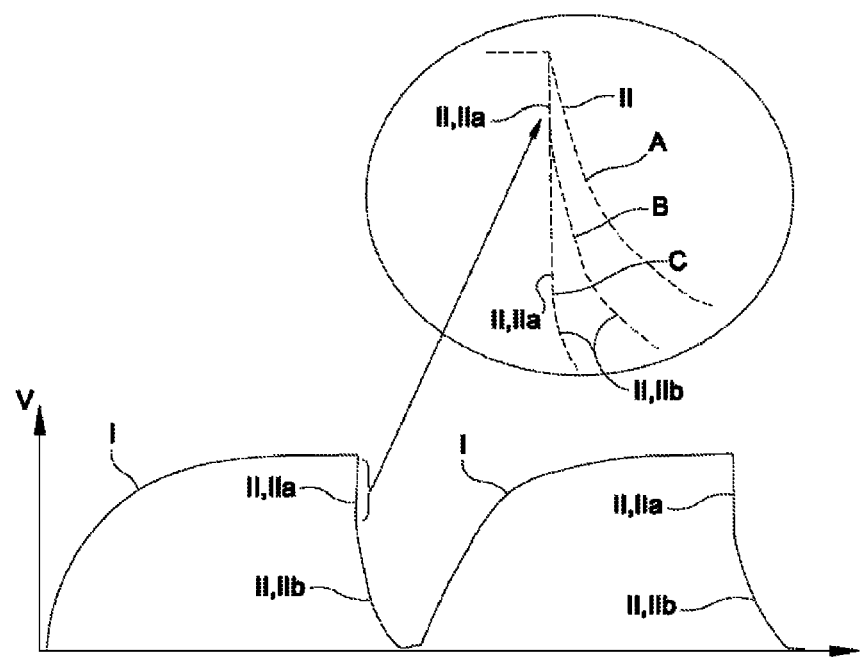
FIG. 6 illustrates a voltage signal when charging and discharging the probe of the system of FIG. 1 according to an embodiment of the present disclosure.

FIG. 6 illustrates two consecutive cycles of exemplary time-dependent voltage signals as measured by the electric circuitry 20 when charging and discharging the probe 2 by periodically performing the above-described first and second steps I, II. The time can be indicated by t, the voltage signal by V. Each cycle can comprise the first step I of charging the probe 2 and the second step II of discharging the probe 2. It, however, can be understood that the cycles can be multiply periodically repeated based on the clock signal 35 having a frequency in the range of from about 1 kHz to about 100 kHz.

In a situation in which the probe tip 4 dips into the bulk liquid 10, starting from a fully discharged probe 2 (V=0) and when charging the probe 2 in the first step (I), the voltage V of the probe 2 can increase exponentially to asymptotically approach a fixed voltage level, inter alia, defined by the capacitive coupling between the probe 2 and the ambient. The increasing portion of the voltage signal denoted by "I" (corresponding to the first step I) in each cycle of the voltage signal can be described by the following formula A:

$$U=U_0*(1-e^{-t/R \cdot C_{mess}}) \quad (A)$$

wherein t can be the time, U can be the measured voltage, R can be the sum of the resistances $R_1$, $R_2$ of the first and second resistors 31, 32 and the measured resistance $R_{mess}$ of the sample 30 which can be greatly different in case the probe tip 4 dips into the foam 21 and the bulk liquid 10, respectively, ($R=R_1+R_2R_{mess}$), $U_0$ can be a constant voltage value depending on the layout of the system 1, and $C_{mess}$ can be the capacitance of the probe 2. Furthermore, electric inductances can be rather low and, thus, can be neglected.

Then, when discharging the charged probe 2 in the second step II, two characteristic sections of the decreasing portion, denoted as "II" (corresponding to the second step II) of the voltage signal can be observed: a vertical first section IIa and a non-vertical second section IIb.

The first section IIa of the decreasing portion II of the voltage signal can reflect the contribution of the electric resistance $R_{mess}$ of the sample 30 and can be described by the following formula B:

$$U=U_0/(R_2+R_{mess}) \cdot R_{mess} \quad (B)$$

wherein U can be the measured voltage, $U_0$ can be a constant voltage value, $R_2$ can be the resistance of the second resistor 32 and $R_{mess}$ can be the measured electric resistance of the sample 30.

The following second section IIb of the decreasing portion II of the voltage signal can be described by the following formula C:

$$U=U_{start}*(e^{-t/R \cdot C_{mess}}) \quad (C)$$

wherein t can be the time, R can correspond to the sum of the electric resistance $R_2$ of the second resistor 32 and the measured electric resistance $R_{mess}$ of the sample 30 and $C_{mess}$ can be the capacitance of the probe 2. Furthermore, $U_{start}$ can be given by the formula D:

$$U_{start}=U_0/(R_2+R_{mess}) \cdot R_2 \quad (D)$$

wherein the symbols can have the same meaning as above.

FIG. 6 also includes an enlarged view of the decreasing portion II of the voltage signal (indicated as "B"). For the reason of comparison, the enlarged view can also contain the decreasing portion II (indicated as "A") which can occur when the probe tip 4 is outside the sample 30 and the decreasing portion II of a voltage signal which can be obtained when the probe tip 4 is in the foam 21 (indicated as "C").

Accordingly, as can be taken from the enlarged view of the decreasing portion II of the various voltage signals, the decreasing portion II can be greatly different in case
  the probe tip 4 is outside the sample 30 (curve A)
  the probe tip 4 is in the bulk fluid 10 (curve B)
  the probe tip 4 is in the foam 21 (curve C)

In the case where the probe tip 4 is outside the sample 30 (curve A), due to the fact that the electric resistance $R_{mess}$ of the probe 2 can be neglected ($R_{mess}$=0), the second portion II (decreasing flank) of each cycle can be comparably shallow without having a vertical section IIa, in other words, only having the second section IIb. Alternatively, in case the probe tip 4 is in the bulk liquid 10 (curve B), the measured electric resistance ($R_{mess}$) can correspond to that one of the bulk liquid 10 ($R_{mess}$>0) so that the second portion II (decreasing flank) of each cycle can include a vertical portion IIa. Yet alternatively, in case the probe tip 4 is in the foam 21 (curve C), the measured electric resistance $R_{mess}$ of the sample 30 can be higher than in the case of being in the bulk liquid 10 ($R_{mess}$>>0) so that the second portion II (decreasing flank) of each cycle can include a vertical portion IIa which can be longer than in curve B.

Accordingly, by analyzing the second portion II (decreasing flank) of each cycle of the voltage signal with respect to the measured electric resistance $R_{mess}$ of the sample 30, in particular with respect to the length of the vertical portion IIa thereof, a change of the measured electric resistance $R_{mess}$ of the sample 30 can be observed so that foam 21 can readily be discriminated from the bulk liquid 10. Specifically, the length of the vertical portion IIa can, for example, be compared with a pre-defined reference value to discriminate between foam 21 and bulk liquid 10. In the same manner, based on the length of the vertical portion IIa which can be longer in the case where the probe tip 4 is in contact with the residuals 48 of the bulk liquid 10 than in the case where the probe tip 4 is in contact with the bulk liquid 10, the bulk liquid 10 can reliably be discriminated from the residuals 48 thereof.

Furthermore, by detecting the change of electric resistance $R_{mess}$ of the sample 30, as reflected by a change of the length of the first section IIa of the decreasing portion II by repeatedly performing the above-described pair of first and second steps, it can be detected at which position of the probe 2 the probe tip 4 hits the liquid surface 11 so as to detect the liquid surface 11. Hence, by sampling the voltage signal and/or a time derivative thereof, the electric resistance $R_{mess}$ measured via the probe 2 can also be used to detect the liquid surface 11.

The above process can be performed when lowering the probe 2 towards the sample 30, for example, to position the probe tip 4 within the bulk liquid 10 for performing a pipetting operation. It, however, can be also possible to detect the liquid surface 11 without performing a pipetting operation.

Figure 7A:
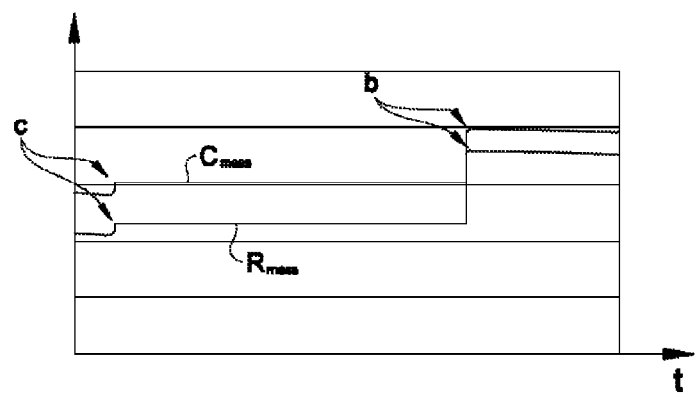
FIGS. 7A-C illustrate exemplary variations of resistance and capacitance of the probe of the system of FIG. 1 according to an embodiment of the present disclosure.
Figure 7B:
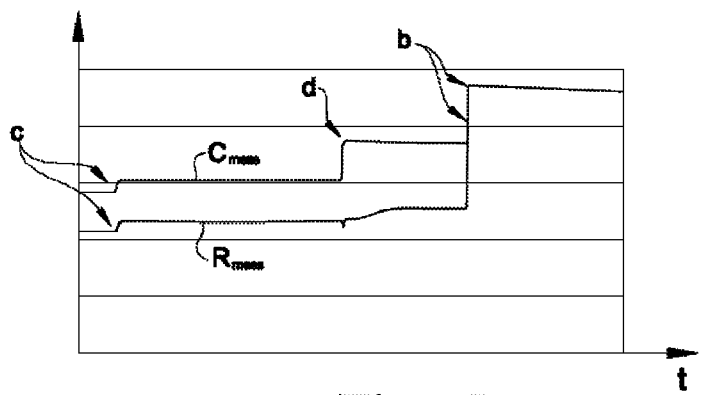
Figure 7C:
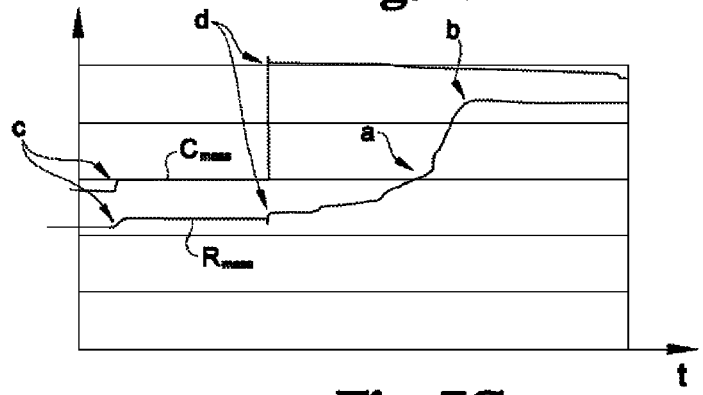

Reference is now made to FIGS. 7A-7C depicting exemplary variations of the electric resistance and capacitance of the probe 2 of the system of FIG. 1 when lowering the probe 2 into the sample 30 (for example, blood serum) contained in the top-closed tube 44 illustrated in FIG. 2. In each diagram, the time (t)-dependent variation of the electric resistance $R_{mess}$ measured via the probe 2 and electric capacitance $C_{mess}$ of the probe 2 is illustrated. The electric resistance $R_{mess}$ and electric capacitance $C_{mess}$ can be respectively given in arbitrary units. FIGS. 7A-7C illustrate only the downwards movement of the probe 2. Specifically, the probe 2 can be moved through an opening (not shown in FIG. 2) of the cap 45 or can be sharpened to penetrate the cap 45.

A typical process may start from a situation in which the probe 2 is located in a first position right above the sample vessel 7. In the case where the probe 2 is located in a position other than the first position, for example, by virtue of a preceding pipetting operation, the probe 2 can be moved into the first position by the positioning mechanism 9. Accordingly, the process may include positioning the probe 2 into the first position right above the sample vessel 7.

Next, the clock signal 35 can be activated resulting in a periodically repeated execution of the first and second steps for charging and discharging the probe 2. Synchronously, the sampling device 22 can be operated so as to detect the voltage signal applied to and received from the probe 2 to obtain the electric resistance $R_{mess}$ of the sample 30. Continuously applying the clock signal 35, the probe 2 can be lowered into the sample 30 until the electric resistance $R_{mess}$ of the sample 30 indicates that the probe tip 4 in in the bulk liquid 10 and then can be lifted upwards to be outside the sample 30.

Specifically, FIG. 7A relates to a situation in which the sample 30 comprises only of bulk liquid 10 (i.e., no foam 21 present on the liquid surface 11) and residuals 48 such as drops on lower side of the cap 45, for example, due to sample 30 or condensed water being attached thereon. In this case, when lowering the probe 2 from the atmosphere into the sample 30, in a position denoted as "c", due to the wet cap 45 a slight change both of the electric resistance $R_{mess}$ measured via the probe 2 and the electric capacitance $C_{mess}$ of the probe 2 can be observed. When further lowering the probe 2 into the sample 30, a much larger change of both the electric resistance $R_{mess}$ and the electric capacitance $C_{mess}$ can be observed when the probe tip 4 hits the bulk liquid 10 in a position indicated by "b". A similar behaviour can be observed when the moving direction of the probe 2 is reversed which is not illustrated in FIG. 7A. Accordingly, the wet cap 45 can cause a comparably small change of both the electric resistance $R_{mess}$ and the electric capacitance $C_{mess}$. Otherwise, the bulk liquid 10 can cause a significant change of both the electric resistance $R_{mess}$ and the electric capacitance $C_{mess}$. Accordingly, the electric resistance $R_{mess}$ measured via the probe 2 can be used to discriminate between the residuals 48 and the bulk liquid 10.

FIG. 7B relates to a situation in which the sample 30 comprises of bulk liquid 10 and an overlying second foam zone 49 on the liquid surface 11. Furthermore, the lower side of the cap 45 can be wetted by residuals 48, for example, by drops attached thereon. In this case, when lowering the probe 2 from the atmosphere into the sample 30, in a position denoted as "c", due to the wet cap 45 a slight change both of the electric resistance $R_{mess}$ and the electric capacitance $C_{mess}$ can be observed similar to FIG. 7A. When further lowering the probe 2 into the sample 30, a much larger change of only the electric capacitance $C_{mess}$ of the probe 2 (but not the electric resistance $R_{mess}$) can be observed when the probe tip 4 hits the second foam zone 49 in a position indicated by "d". When further lowering the probe 2 into the sample 30, a much larger change of both the electric resistance $R_{mess}$ and the electric capacitance $C_{mess}$ can be observed when the probe tip 4 hits the bulk liquid 10 in a position indicated by "b". Accordingly, the wet cap 45 can cause a small change of both the electric resistance $R_{mess}$ measured by the probe 2 and the electric capacitance $C_{mess}$ of the probe 2, while the second foam zone 49 can cause a larger change of the electric capacitance $C_{mess}$ of the probe 2 only. Contrary thereto, the bulk liquid 10 can cause a significant change of both the electric resistance $R_{mess}$ measured by the probe 2 and the electric capacitance $C_{mess}$ of the probe 2. Hence, there can be a significant difference between the measured electric resistance $R_{mess}$ and the electric capacitance $C_{mess}$ of the probe 2 since the electric resistance $R_{mess}$ measured by the probe 2 may not be sensitive to the second foam zone 49.

FIG. 7C relates to a situation in which the sample 30 comprises of bulk liquid 10, a first foam zone 46 and a second foam zone 49 on the liquid surface 11 and, furthermore, the lower side of the cap 45 can be wetted by residuals 48 such as drops of the bulk liquid 10. In this case, when lowering the probe 2 from the air into the sample 30, in a position denoted as "c", due to the wet cap 45 a slight change both of the electric resistance $R_{mess}$ and the electric capacitance $C_{mess}$ can be observed similar to FIGS. 7A and 7B. When further lowering the probe 2 into the sample 30, a much larger change of only the electric capacitance $C_{mess}$ of the probe 2 (but not the electric resistance $R_{mess}$ of the sample 30 measured by the probe 2) can be observed when the probe tip 4 hits the second foam zone 49 in a position indicated by "d" similar to FIG. 7B. When further lowering the probe 2 into the sample 30, the electric capacitance $C_{mess}$ of the probe 2 can remain unchanged while a slight change of the electric resistance $R_{mess}$ of the sample 30 can be observed when the probe tip 4 hits the first foam zone 46 in a position indicated by "a" and a much larger change of the electric resistance $R_{mess}$ can be observed when the probe tip 4 hits the bulk liquid 10 in a position indicated by "b". Accordingly, the wet cap 45 can cause a small change of both the electric resistance $R_{mess}$ and the electric capacitance $C_{mess}$, while the second foam zone 49 can cause a larger change of the electric capacitance $C_{mess}$ of the probe 2 only. Since there is no change of the electric capacitance $C_{mess}$ of the probe 2 when the probe tip 4 hits the first foam zone 46 and the bulk liquid 10, respectively, the second foam zone 49 can neither be discriminated from the first foam zone 46 nor the bulk liquid 10 by means of the electric capacitance $C_{mess}$ of the probe 2. Otherwise, there is essentially no change of the electric resistance $R_{mess}$ measured via the probe 2 when the probe tip 4 hits the second foam zone 49 but a significant change of the electric resistance $R_{mess}$ measured via the probe 2 when the probe tip 4 hits the bulk liquid 10. Hence, in contrast to the electric capacitance $C_{mess}$ of the probe 2, the electric resistance $R_{mess}$ of the sample 30 measured via the probe 2 can be used to discriminate between the second foam zone 49 and the first foam zone 46 since the electric resistance $R_{mess}$ is not sensitive to the second foam zone 49. Furthermore, the electric resistance $R_{mess}$ can be used to discriminate between the second foam zone 49 and the bulk liquid 10. And, the electric resistance $R_{mess}$ can be used to discriminate between the residuals 48 and the bulk liquid 10.

Accordingly, in the case of having both a first foam zone 46 and/or a second foam zone 49 on the bulk liquid 10, the electric resistance $R_{mess}$ measured by the probe 2 can be used to discriminate between foam 21 and bulk liquid 10. In the case of also having residuals 48 of the bulk liquid 10, the electric resistance $R_{mess}$ measured by the probe 2 can be used to discriminate between residuals 48 and bulk liquid 10. Thus, the process can be considered superior to conventional methods based on capacitance detection.

Accordingly, the probe tip 4 can reliably be positioned within the bulk liquid 10 to aspirate liquid while keeping the probe 2 stationary or, in case of larger volumes, while positioning the probe tip 4 further into the bulk liquid 10 so as to maintain the probe tip 4 in a position below the liquid surface 11.

The clock signal 35 can be applied to both the base contact 18 of the transistor 15 and the electric circuitry 20 can be a medium-frequency voltage signal having a frequency in the range of from about 1 kHz to about 100 kHz. As a result, the voltage signal obtained from the probe 2 can comprise a decreasing flank (decreasing portion II) having a steepness ideal for determining the electric resistance $R_{mess}$ of the sample 30. In the case of using a clock signal 35 comprising voltage pulses having a frequency in a range below about 1 kHz, foam 21 and bulk liquid 10 can be considered as a single "conductive unit" so that foam 21 and bulk liquid 10 cannot be reliably discriminated by their conductance (very shallow flanks). Otherwise, when using a clock signal 35 comprising voltage pulses having a frequency of more than about 100 kHz, there can also be no clear distinction between foam 21 and bulk liquid 10 possible (very steep flanks).

In the system 1, the controller 34 can be set up to control positioning of the probe 2 based on the electric resistance $R_{mess}$ of the sample 30. The controller 34 may, for example, be embodied as programmable logic device (microprocessor) running a computer-readable program provided with instructions to perform operations in accordance with a predetermined process routine. The controller 34 can be electrically connected to the various system components which require control and/or provide information which include the positioning mechanism 9 for positioning the probe 2.

In one embodiment, the probe 2 can be made of electrically conductive material such as, for example, a metal such as stainless steel. Furthermore, the sample vessel 7 and/or the work-plate 8 can be made of electrically isolating material such as, for example, plastics.

In one alternative embodiment, instead of charging the probe 2 in the first step I until a fixed voltage is reached, charging can also be performed for a predetermined time-interval. In another alternative embodiment, instead of detecting the electric voltage when discharging the probe 2, the time for (fully) discharging the probe 2 can be determined. In yet another alternative embodiment, determining the electric resistance $R_{mess}$ of the sample 30 via the probe 2 can be combined with determining the capacitance change typically occurring when the probe tip 4 dips into the sample 30. This can especially be useful in case of very small sample volumes.

Figure 8A:
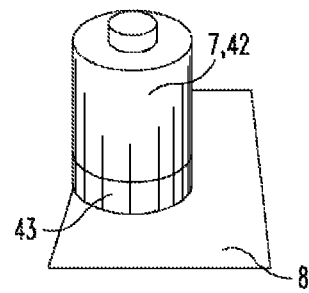
FIGS. 8A-B illustrate two further exemplary embodiments of the sample vessel of the system of FIG. 1 according to an embodiment of the present disclosure.

With reference to FIG. 8A, the sample vessel 7 can, for example, comprise an electrically isolating portion 42 made of isolating material such as, for example, plastics and an electrically conductive portion 43 made of electrically conductive material such as, for example, an electrically conductive plastics, the latter one being used to place the sample vessel 7 on a grounded work-plate 8 made of electrically conductive material such as, for example, a metal.

Figure 8B:
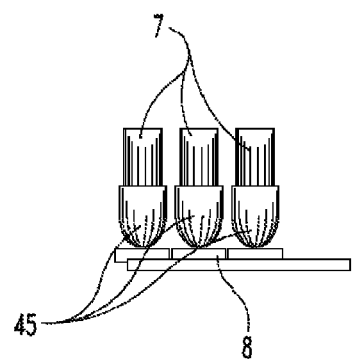

With reference to FIG. 8B, the sample vessel 7 can, for example, comprise an electrically isolating tube 44 made of isolating material such as, for example, plastics put in a conductive capsule 45 made of electrically conductive material such as, for example, an electrically conductive plastics, the latter one being used to place the sample vessel 7 on a grounded work-plate 8 made of electrically conductive material such as, for example, a metal.

Sample vessels 7 as illustrated in FIGS. 8A and 8B can be used to improve the capacitive coupling between the probe 2 and the work-plate 8 for measuring the electric resistance of the probe 2. By increasing the capacitive coupling therebetween, the number of charge carriers for charging the probe 2 can be increased so as to improve the signal strength of the electric signal obtained from the probe 2.

In the system 1, the foamy portion of the sample 30 as well as residuals 48 of the bulk liquid 10 can be reliably discriminated from the bulk liquid 10 by a significant change of the electric resistance of the sample 30 measured via the probe 2 as a result of the difference in electric conductivity (electric resistance) between the foam 21 and residuals 48 of the bulk liquid 10 on the one hand, and the bulk liquid 10 on the other hand. Furthermore, the liquid surface 11 of the bulk liquid 10 can also reliably be detected.

It is noted that terms like "preferably," "commonly," and "typically" are not utilized herein to limit the scope of the claimed embodiments or to imply that certain features are critical, essential, or even important to the structure or function of the claimed embodiments. Rather, these terms are merely intended to highlight alternative or additional features that may or may not be utilized in a particular embodiment of the present disclosure.

For the purposes of describing and defining the present disclosure, it is noted that the term "substantially" is utilized herein to represent the inherent degree of uncertainty that may be attributed to any quantitative comparison, value, measurement, or other representation. The term "substantially" is also utilized herein to represent the degree by which a quantitative representation may vary from a stated reference without resulting in a change in the basic function of the subject matter at issue.

Having described the present disclosure in detail and by reference to specific embodiments thereof, it will be apparent that modifications and variations are possible without departing from the scope of the disclosure defined in the appended claims. More specifically, although some aspects of the present disclosure are identified herein as preferred or particularly advantageous, it is contemplated that the present disclosure is not necessarily limited to these preferred aspects of the disclosure.

I claim:

1. A method for discriminating bulk liquid from foam and/or residuals of the bulk liquid of a sample contained in a sample vessel, the method comprising:
    providing a probe having an electric capacitance;
    moving the probe into the sample;

repeatedly performing a pair of consecutive steps of charging and at least partially discharging the probe to generate a discharging current;

measuring a quantity indicative of the discharging current for each pair of consecutive steps of charging and at least partially discharging the probe;

analyzing the quantity to determine an electric resistance ($R_{mess}$) of the sample via the probe; and discriminating the bulk liquid from the foam and/or the residuals of the bulk liquid based on a change of the electric resistance ($R_{mess}$ of the sample that is detected by a change of length of a vertical section of a decreasing portion of a voltage signal occurring when the probe passes from outside the sample through the foam and contacts the bulk liquid.

2. The method according to claim 1, wherein the pair of consecutive steps of charging and at least partially discharging the probe is periodically repeated with a repeating frequency in a range of from 1 kHz to 100 kHz.

3. The method according to claim 1, wherein the quantity indicative of the discharging current of the probe is an electric voltage signal and/or a time derivative thereof obtained when discharging the probe.

4. The method according to claim 3, wherein the electric voltage signal is sampled simultaneously with discharging the probe.

5. The method according to claim 3, wherein the electric voltage signal is analyzed with respect to a voltage drop at the beginning of discharging the probe.

6. The method according to claim 1, wherein the quantity indicative of the discharging current is a time interval required for fully discharging the probe.

7. The method according claim 1, wherein a liquid surface of the bulk liquid is determined based on the change of the electric resistance ($R_{mess}$) of the sample.

8. The method according to claim 1, wherein an electric capacitance ($C_{mess}$) of the probe is determined for each pair of consecutive steps of charging and at least partially discharging the probe.

9. A method for positioning a probe having an electric capacitance for performing pipetting operations on a sample, the method comprising:

providing a probe having an electric capacitance;

moving the probe into a sample;

repeatedly performing a pair of consecutive steps of charging and at least partially discharging the probe to generate a discharging current;

measuring a quantity indicative of the discharging current for each pair of consecutive steps of charging and at least partially discharging the probe and analyzing the quantity to determine an electric resistance ($R_{mess}$) of the sample;

discriminating bulk liquid from foam and/or residuals of the bulk liquid based on a change of the electric resistance ($R_{mess}$) of the sample that is detected by a change of length of a vertical section of a decreasing portion of a voltage signal occurring when the probe passes from outside the sample through the foam and contacts the bulk liquid; and positioning the probe in the bulk liquid based on the change of the electric resistance ($R_{mess}$) of the sample.

10. The method according to claim 9, wherein the probe is moved further into the bulk liquid when aspirating the bulk liquid.

11. An automated system for discriminating bulk liquid from foam and/or residuals of the bulk liquid of a sample contained in a sample vessel, the automated system comprising:

at least one probe having an electric capacitance;

a positioning mechanism for moving the probe relative to the sample;

a voltage source of a fixed voltage for charging the probe;

an electric drain for discharging the probe to generate a discharging current;

a controllable switch to alternatively connect the probe to the voltage source or to the drain;

an electric circuitry connected to the probe to measure a quantity indicative of the discharging current;

a controller to move the probe into the sample, to control the switch to repeatedly perform consecutive steps of charging and at least partially discharging the probe, and to control the electric circuitry to measure the quantity indicative of the discharging current for each pair of consecutive steps of charging and at least partially discharging the probe to determine an electric resistance ($R_{mess}$) of the sample, wherein bulk liquid is discriminated from foam and/or residuals of the bulk liquid based on a change of the electric resistance ($R_{mess}$) of the sample that is detected by a change of length of a vertical section of a decreasing portion of a voltage signal occurring when the probe passes from outside the sample through the foam and contacts the bulk liquid.

12. The system according to claim 11, wherein the electric circuitry comprises a sample-and-hold device for sampling a voltage signal and/or a time derivative thereof obtained when discharging the probe.

13. The system according to claim 11, wherein the probe performs pipetting operations for pipetting liquids.

14. The system according to claim 11, wherein the sample vessel comprises a vessel portion made of an electrically conductive material, the conductive vessel portion being supported by an electrically conductive support electrically connected therewith.

15. The system according to claim 11, wherein the sample vessel is made of isolating material and is accommodated in a vessel envelope made of an electrically conductive material, the conductive vessel envelope being supported by an electrically conductive support electrically connected therewith.

* * * * *